(12) United States Patent
Basile et al.

(10) Patent No.: US 7,074,280 B2
(45) Date of Patent: Jul. 11, 2006

(54) METHOD AND SYSTEM TO REPRESENT A TEMPERATURE EXPERIENCED BY A MEDICAL DEVICE IN A MEDICAL WASHING MACHINE

(75) Inventors: Mark D. Basile, Grosse Pointe, MI (US); Ralph J. Basile, Sterling Heights, MI (US); Steven J. Basile, Grosse Pointe Woods, MI (US)

(73) Assignee: Healthmark Industries Co., St. Clair Shores, MI (US)

( * ) Notice: Subject to any disclaimer, the term of this patent is extended or adjusted under 35 U.S.C. 154(b) by 307 days.

(21) Appl. No.: 10/613,276

(22) Filed: Jul. 3, 2003

(65) Prior Publication Data

US 2005/0000548 A1    Jan. 6, 2005

(51) Int. Cl.
*B08B 7/04* (2006.01)

(52) U.S. Cl. .................... 134/18; 134/30; 134/57 D; 134/113

(58) Field of Classification Search ............. 134/18, 134/30, 57 D, 25.1, 25.4, 25.2, 113; 422/56
See application file for complete search history.

(56) References Cited

U.S. PATENT DOCUMENTS

| | | | |
|---|---|---|---|
| 2,308,087 A * | 1/1943 | Lappala | 116/216 |
| 3,324,723 A * | 6/1967 | Ritchie et al. | 116/217 |
| 4,232,552 A * | 11/1980 | Hof et al. | 374/106 |
| 4,353,990 A * | 10/1982 | Manske et al. | 435/287.4 |
| 4,410,493 A * | 10/1983 | Joslyn | 422/58 |
| 4,448,750 A | 5/1984 | Fuesting | |
| 4,779,995 A | 10/1988 | Santacaterina | |
| 4,878,588 A * | 11/1989 | Ephraim | 215/11.2 |
| 4,975,246 A | 12/1990 | Charm | |
| RE34,515 E * | 1/1994 | Foley | 374/160 |
| 5,282,683 A | 2/1994 | Brett | |
| 5,380,369 A | 1/1995 | Steinhauser et al. | |
| 5,404,834 A * | 4/1995 | Murphy | 116/216 |
| 5,425,815 A | 6/1995 | Parker et al. | |
| 5,453,245 A | 9/1995 | Kirschner et al. | |
| 5,539,673 A | 7/1996 | Charm et al. | |
| 5,676,465 A | 10/1997 | Witonsky et al. | |
| 5,759,486 A * | 6/1998 | Peterson | 422/21 |
| 6,257,759 B1 | 7/2001 | Witonsky et al. | |
| 6,461,037 B1 | 10/2002 | O'Leary | |
| 6,488,890 B1 * | 12/2002 | Kirckof | 422/56 |
| 6,491,774 B1 | 12/2002 | Witonsky et al. | |

FOREIGN PATENT DOCUMENTS

WO    WO 95/24622 A1 *    9/1995

* cited by examiner

*Primary Examiner*—Alexander Markoff
(74) *Attorney, Agent, or Firm*—Brooks Kushman P.C.

(57) ABSTRACT

A method and system to represent surface temperatures. The method and system represent a surface temperature experienced by a medical device during a washing cycle in a medical washing machine. A temperature strip is positioned proximate a surface of the medical device to represent the surface temperature experienced by the medical device during the washing cycle in the medical washing machine.

16 Claims, 2 Drawing Sheets

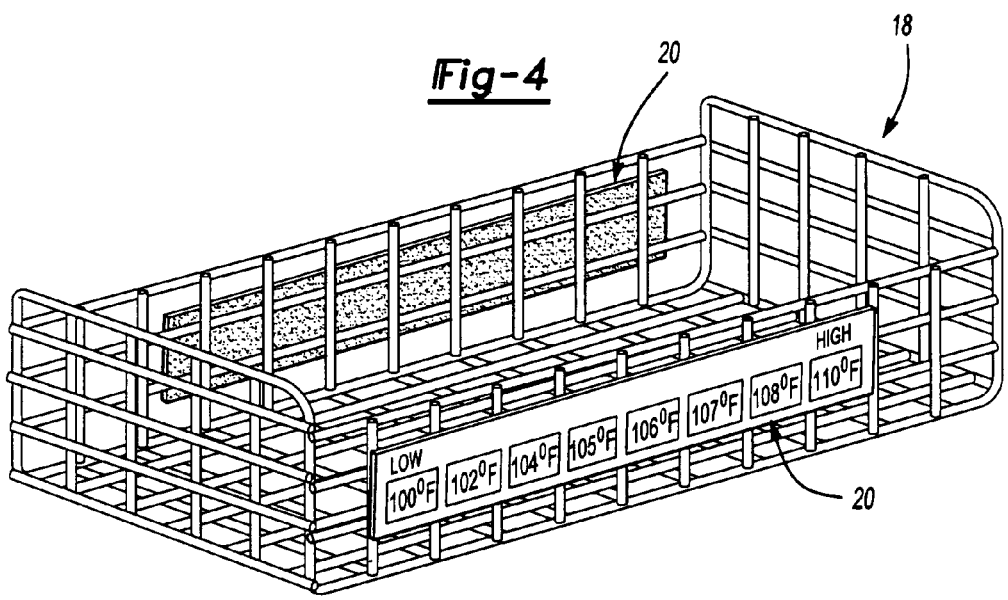
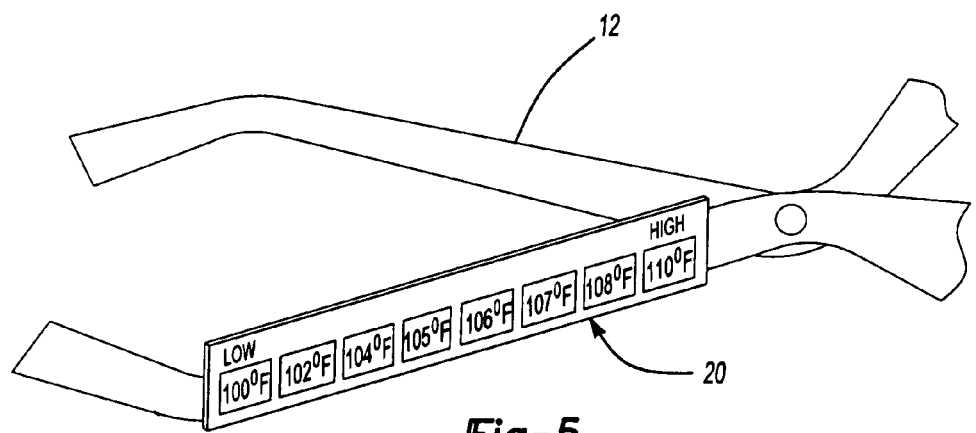

METHOD AND SYSTEM TO REPRESENT A TEMPERATURE EXPERIENCED BY A MEDICAL DEVICE IN A MEDICAL WASHING MACHINE

BACKGROUND OF THE INVENTION

1. Field of the Invention

In general, the present invention relates to methods and system to represent surface temperatures. In particular, the present invention relates to representing a surface temperature experienced by a medical device during a washing cycle in a medical washing machine.

2. Background Art

Medical equipment requires periodic washing to remove contaminations. Medical washing machines wash the medical equipment to remove the contaminants. A typically medical washing cycle may comprise a cold water cycle, an enzyme cycle, a detergent cycle, a disinfection cycle, and an ultrasonic.

A temperature of the fluid in each cycle affects a surface temperature of the medical device. The surface temperature of the medical device affects the ability of the washing cycle to wash away the contaminates. For example, protein can bake onto the medical device in the cold water cycle if the fluid temperature is greater than a predefined level.

The fluid temperature is controlled to remain below the predefined level to prevent the baking. To do so, however, the surface temperature experienced by the medical device during the washing cycle is needed in order to check the fluid temperature and to make any necessary adjustments. Accordingly, there exists a need to represent the surface temperature of a medical device during a washing cycle in a medical washing machine.

A temperature probe can be positioned relative to the medical device to indicate the temperature of the washing fluid. The surface temperature of the medical device can be represented from the probe's indication of the fluid temperature. In particular, an assumption is made that the proximity of the probe to the medical device is sufficient to permit using the probe to represent the surface temperature of the medical device.

One problem with the temperature probe is that the mechanical nature of the temperature probe requires constant calibration and maintenance to prevent malfunctioning. This problem is further complicated with the continuous calibration and maintenance of the medical washing machine. In essence, double tolerancing can occur to limit the accuracy of the temperature probe.

Another problem with the temperature probe is that the temperature probe tends to be difficult to position close to the surface of the medical device. A gap can arise wherein the fluid temperature measured by the temperature probe may be different than the fluid temperature at the surface of the medical device. Moreover, even if the probe is positioned close to the medical device, the probe tends to obstruct a fluid flow prior to the fluid reaching the surface of the medical device. This can cause the surface temperature of the medical device to differ from the fluid temperature indicated by the probe and prevent the probles from mimicing the washing felt by the medical device.

SUMMARY OF THE INVENTION

The present invention provides a method and system to represent a surface temperature experienced by a medical device during a medical washing cycle in a medical washing machine. The present invention overcomes the problems identified above with respect to a temperature probe by positioning a thermometer strip proximate a surface of the medical device.

One aspect of the present invention relates to a method to indicate a peak surface temperature experienced by the medical device during the medical washing cycle. The method comprises inserting the medical device, positioning the thermometer strip, and indicating a peak thermometer temperature.

Positioning the thermometer strip comprises positioning the thermometer strip proximate the surface of the medical device. The proximity of the thermometer to the surface of the medical device permits the peak temperature of the thermometer to represent the peak surface temperature of the medical device. The positioning of the thermometer can comprise affixing the thermometer directly to the medical device, affixing the thermometer to a tray used to support the medical device, or to rack used to support the tray.

Indicating the thermometer temperature comprises viewing a temperature display of the thermometer strip. The temperature display includes a predefined range of temperature sections. Each temperature section includes a temperature value indicator. The indicator becomes visible if the temperature corresponds with that section. One example of such a thermometer strip is a LCD thermometer strip.

The thermometer display can be reversible or irreversible. The reversible display constantly changes the displayed temperature according to the present temperature. In contrast, the irreversible thermometer only displays increases in temperature relative to a low temperature limit. With respect to the reversible thermometer, indicating the peak thermometer temperature comprises continuous viewing of the thermometer display during the washing cycle. With respect to the irreversible thermometer, indicating the peak thermometer temperature comprises viewing the thermometer display after the washing cycle.

One aspect of the present inventions relates to a system to wash medical equipment. The system comprises a medical washing machine. The medical washing machine can execute a washing cycle to wash away contaminants. The washing cycle can comprises a number of individual washing cycles, such as one or more of a cold water cycle, an enzyme cycle, a detergent cycle, a disinfection cycle, and an ultrasonic cycle. The system further comprises a tray to support the medical equipment in the medical washing machine. The tray can be a plastic tray or a wire mesh. The system further comprises a thermometer strip affixed proximate a surface of the medical device. The thermometer strip indicates a thermometer temperature proximate the surface of the medical device. The thermometer temperature represents the surface temperature of the medical device

BRIEF DESCRIPTION OF THE DRAWINGS

FIG. 4 illustrates a positioning of the thermometer shown in FIG. 3 when affixed to an exemplary tray shown in FIG. 2; and FIG. 5 illustrates a positioning of the thermometer shown in FIG. 3 when affixed to the medical device.

DETAILED DESCRIPTION OF THE PREFERRED EMBODIMENT(S)

Figure 1:
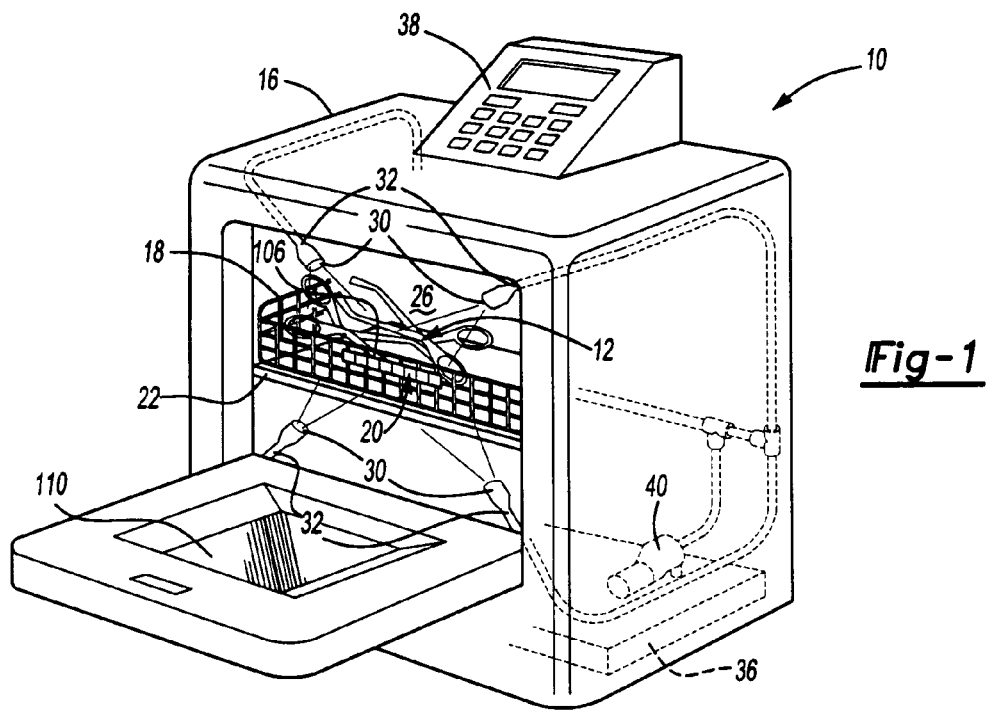
FIG. 1 illustrates a system to wash a medical device.

FIG. 1 illustrates a system 10 to wash a medical device 12. The system 10 comprises a medical washing machine 16, a tray 18, and a thermometer strip 20. The medical device 12 is placed in the tray 18 and the tray 18 is place in the washing machine 16 for washing.

The washing machine 16 comprises any medical washing machine. The washing machine 16 can be used to wash any medical device 12, including all types of surgical instrumentation, including forceps, scissors, orthopedic implants, and light handle covers. The washing machine shown includes one or more racks 22 within a washing chamber 26 to support the tray 18 during washing.

The medical washing machine 16 provides fluid to wash the medical device. The fluid can be provided in a washing cycle. Any arrangement of nozzles 30 and sprayers 32 can be used to deliver fluid to the washing chamber 26. These nozzles 30 and sprayers 32 can deliver water and cleaning solution. The nozzles 30 rotate using mechanical as well as chemical action to wash the medical device 12. The washing machine 16 includes chambers 36 to heat and control fluid delivery, a key pad 38 for direction of washing cycles, and various pumps 40 for delivering water and cleaning solution. Normally the racks 22 are removable for easy loading and unloading of the medical device 12.

Figure 2:
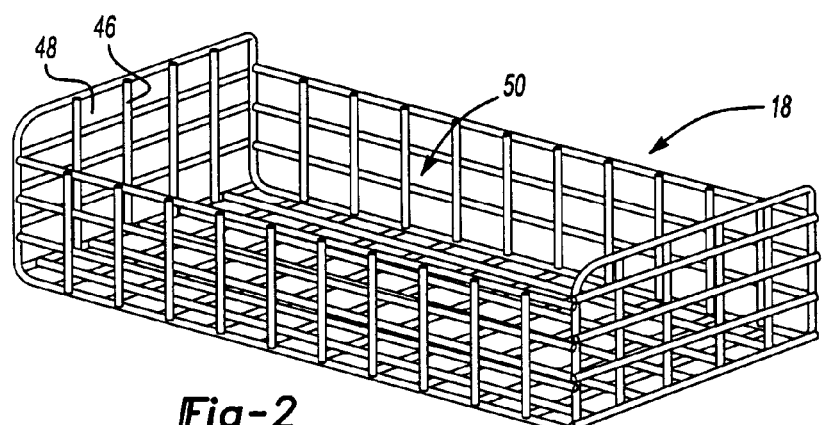
FIG. 2 illustrates a tray to support the medical device during a washing cycle.

FIG. 2 illustrates the tray 18. The tray 18 can be used to support the medical device 12 during washing. The tray 18 comprises a wire mesh portion 46 to permit fluid to flow through openings 48. The openings 48 permit the fluid to reach the medical device 12 for washing. The tray 18 can comprise any number of materials, such as plastics, nylons, and metals. The tray 18 can also comprise a unitary construction (not shown) where the wire mesh openings are filled in with material.

Figure 3:
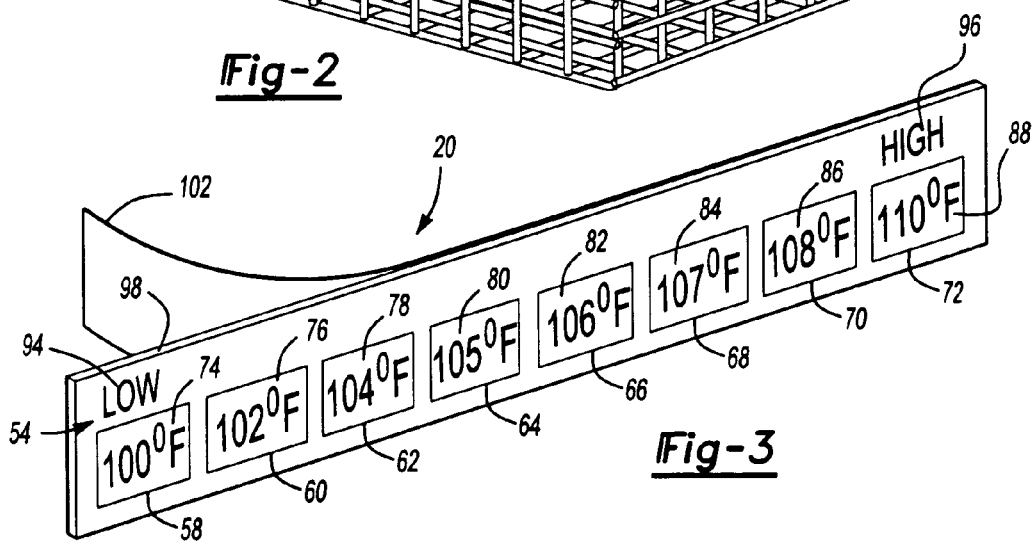
FIG. 3 illustrates a thermometer strip to measure a surface temperature experienced by the medical device during a washing cycle.

FIG. 3 illustrates the thermometer strip 20. The thermometer strip 20 includes a temperature display 54. The temperature display 54 includes a predefined range of temperature sections, eight temperature sections, 58, 60, 62, 64, 66, 68, 70, 72, are shown. More of less temperature sections can be used. Each temperature section includes a temperature indicator 74, 76, 78, 80, 82, 84, 86, 88. The indicator becomes visible if the temperature corresponds with that section. One example of such a thermometer strips is a liquid crystal display (LCD) thermometer strip.

The temperature sections are divide up between a low temperature limit 94 and a high temperature limit 96. Any number of temperature indicators can be displayed in any number of increments between the low temperature limit 94 and the high temperature limit 96. In some cases, it may be desirable to include a relatively narrow temperature range with minor increments in temperature values, and in some cases, it may be desirable to include relatively larger temperature ranges with larger increments in temperature values. In addition, the temperature increments can vary. For example, temperature increments of 2° can be displayed around the low limit and decrease to 1° F. increments around the high limit.

The thermometer display 54 can be reversible or irreversible. The reversible thermometer constantly changes the displayed temperature to the present temperature. Typically, such a change requires the temperature to occur for a predetermined period of time to prevent instantaneous changes in the displayed temperature. The irreversible thermometer only displays temperature increases relative to the low temperature limit 44. As such, only the peak temperature is displayed.

The thermometer strip 20 preferably includes an adhesive material layer 98 and an adhesive layer covering 102. The adhesive covering layer 102 is removable to expose the adhesive layer 98. The adhesive layer 98 is suitable to affix the thermometer strip 20 to the tray 18. The adhesive layer 98 can also be suitable to affix the thermometer to the medical device 12. Different types of adhesive layers 102 may be required depending on whether the thermometer strip 20 is affixed to the tray 18 or the medical device 12. In addition, different types of adhesive layers 102 may be required for different washing cycles.

FIG. 4 illustrates the positioning of multiple thermometer strip 20 when affixed to the tray 18. FIG. 5 illustrates the positioning of the thermometer strip 20 when affixed to the medical device 12. The thermometer strip 20 is preferably positioned close enough to a surface 106 of the medical device 12 that the displayed temperature corresponds with the surface temperature of the medical device 12. As such, the thermometer strip 20 can be positioned to the sides or bottom of the tray 18, directly to the medical device 12, or in any other position proximate the medical device 12, such as to the rack 22.

The proximity of the thermometer strip 20 to the medical device 12 increases the ability the thermometer strip 20 to mimic the surface 106 of the medical device 18. This is key because the fluid that is measured at one point in the chamber can be dramatically different than that at the surface 106. For example, one or more of sprayers 32 may be clogged and therefore no fluid reaches the medical device 12, or there is so many medical devices 12 in the washing chamber that they obstruct the flow of fluid to change the fluid temperature before the fluid reaches the medical device 12, or a myriad of other possibilities. These and other problems can cause the measured fluid temperature to differ from the surface temperature of the medical device 12 if the thermometer strip 20 fails to be positioned proximate to the medical device 12.

Returning to FIG. 1, the medical washing machine 16 preferably executes one or more fluid washing cycles to wash the medical device. The washing cycles can include a cold water cycle, an enzyme cycle, a detergent cycle, a disinfection cycle, and an ultrasonic cycle. In some cases, however, the ultrasonic cycle may be done with a separate ultrasonic cleaner.

The cold water cycle includes washing the medical device 12 with relatively cold water. Preferably, the fluid temperature is sufficiently controlled to maintain the exposed outer surfaces of the medical device within a surface temperature range of 100° F. to 110° F., but not exceeding 110 F. Fluid temperatures in excess of 110° F. can cause the contaminants to bake onto the medical equipment.

The enzyme cycle includes washing the medical device 12 with a enzyme containing fluid. Preferably, the fluid temperature is sufficiently controlled to maintain the exposed outer surfaces of the medical device within a surface temperature range of 110° F. to 130° F., but not exceeding 130° F. Fluid temperatures in excess of 130° F. can breakdown the enzymes to render the enzymes ineffective at breaking down proteins on the medical device.

The detergent cycle includes washing the medical device with a detergent containing fluid. Preferably, the fluid temperature is sufficiently controlled to maintain the exposed outer surfaces of the medical device within a surface temperature range of 140° F. to 150° F., but not exceeding 150°

F. Fluid temperatures in excess of 150° F. can breakdown the detergent to render the detergent ineffective at breaking down proteins on the medical device.

The disinfection cycle includes washing the medical device 12 with a disinfectant containing fluid. Preferably, the fluid temperature is sufficiently controlled to maintain the exposed outer surfaces of the medical device 12 within a surface temperature range of 170° F. to 180° F., even though greater temperatures are acceptable. The disinfecting cycle is sometimes referred to as a high temperature water kill because of the acceptable higher temperatures. Fluid temperatures below 170° F. are monitored because the fluid fail to disinfect below 170° F.

The ultrasonic cycle includes washing the medical device 12 with a fluid at a particular frequency. Preferably, the fluid temperature is sufficiently controlled to maintain the exposed outer surfaces of the medical device within a surface temperature range of 100° F. to 110° F., but not exceeding 110° F., if enzymes are used, and 120° F. to 130° F., but not to exceed 130° F., if alkaline detergent is used. An ultrasonic cycle is designed to break away the contaminants and the detergent helps with the cavitation action to break away the contaminants. They work in tandem, and if the temperature is too high or too low they are less effective in creating the right action and protein breakdown.

An optional manual soaking cycle includes washing the medical device 12 in a container (not shown) having fluid. The manual soaking cycle helps to remove any loose contaminants and to remove any remaining cleaning fluid. The container is separated from the medical washing machine 16 so that an operator remove the medical device 12 from the medical washing machine 16. Once removed, the medical device 12 can be dipped into the container. Preferably, the fluid temperature is sufficiently controlled to maintain the exposed outer surfaces of the medical device within a surface temperature range of 90° F. to 110° F. If the temperature of the detergents or enzymes are not correct then their cleaning action is either compromised or eliminated.

As describe above, each fluid cycle includes a desired surface temperature for the medical device. One application of the present invention relates to a method of measuring the surface temperature of the medical device 12. The method can be used in calibrating the medical washing machine 16 to facilitate achieving the desired surface temperature ranges for the washing cycles.

The calibration generally comprises inserting the medical device 12 into the medical washing machine 16 for a washing cycle and determining the surface temperature of the medical device 12. Typically, the medical device 12 is placed in the tray 18 and the tray 18 and medical device 12 are inserted together into the medical washing machine 16 to begin the calibration.

The thermometer strip 20 is positioned proximate the medical device 12 to represent the surface temperature experience by the medical device 12 during the washing cycle. The positioning of the thermometer strip comprises affixing the thermometer strip 20 to one of the tray 18 or the medical device 12. The thermometer strip 20 can be affixed prior to inserting the medical device 12 or after the medical device 12 is inserted into the washing machine 16.

In some cases, especially in large chamber washing machines 16, multiple thermometer strips 20 can be affixed to represent surface temperatures at different portions of the medical device 12. Multiple thermometer strips 20 can also facilitate calibrating multiple nozzles 30 and sprayers 32. Moreover, multiple thermometer strips 20 can be affixed to the tray 18 and the medical device 12 at the same time. This permits a comparison of temperature values based upon the location of the thermometer strip 20.

The surface temperature of the medical device 12 is indicated by the thermometer strip 20. The indicated surface temperature is used to calibrate the washing machine 16. The reversible thermometer strips 20 can be used when it is desired to make in-process calibrations to the medical washing machine 16. In this manner, the fluid temperature can be adjusted during the washing cycle and the effect of the adjustments appears relatively quickly on the thermometer strip 20. Typically, a transparent opening 110 permits the operator to view the thermometer strip 20.

In some medical washing machines 16, such as some conveyer type medical washing machines, it is difficult to view the thermometer strip 20 throughout the washing cycle. Advantageously, the ability of the irreversible thermometer strip 20 to maintain the peak thermometer temperature permits the peak temperature to be measured when the thermometer is difficult to view throughout the washing cycle.

The calibration of each washing cycle can cover a wide range of desired surface temperatures. The thermometer strip 20 can be configured to any number of different temperature ranges and temperature increments to match the different washing cycles. Typically, the calibration of each individual washing cycle requires removing and replacing the thermometer strip after each washing cycle and selecting a different thermometer strip 20 to match the next washing cycle.

A material of the tray 18 can be selected to match with a material of the medical device 12. The matches of material results in the tray 18 mimicking the medical device 12. The mimicking can enhance the accuracy of the thermometer strip 20 especially when the thermometer strip is affixed to the tray 18. For example, a stainless steel tray can be used with a stainless steel medical device. This way, the effect of the fluid temperature of the stainless steel tray should mimic the effect of the fluid temperature on the stainless steel medical device to enhance accuracy. In addition, the matching can include matching the shape of the tray to the shape of the medical device, and matching the material thickness of the tray to the surface material thickness.

The present invention, as described above, provides a method and system to represent a surface temperature experienced by a medical device during a medical washing cycle in a medical washing machine. The present invention overcomes the problems identified above with respect to a temperature probe by positioning a thermometer strip proximate a surface of the medical device.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of calibrating a washing machine to wash a medical device, the method comprising:

inserting the medical device into the washing machine for a washing cycle;

positioning a disposable thermometer strip proximate the medical device;

measuring a peak temperature of the medical device with the thermometer strip during the washing cycle;

adjusting operation of the washing machine as a function of the measured peak temperature so as to calibrate the washing machine to perform the same washing cycle at a different temperature.

2. The method of claim 1 wherein the thermometer is positioned proximate a surface of the medical device prior to inserting the medical device into the medical washing machine, wherein the thermometer and the medical device are inserted into the medical washing machine at the same time.

3. The method of claim 1 wherein measuring the peak temperature comprises reading the peak thermometer temperature from an irreversible thermometer strip after completion of the first washing cycle.

4. The method of claim 1 wherein measuring the peak temperature comprises viewing the thermometer during the first washing cycle and recording the peak thermometer temperature.

5. The method of claim 1 wherein positioning the thermometer comprises affixing the thermometer to a tray used to support the medical device during the washing cycle.

6. The method of claim 5 wherein the surface of the medical device comprises a first material and the method further comprises matching a tray material to the first material.

7. The method of claim 6 wherein the thermometer includes an adhesive material layer and an adhesive layer covering, and wherein positioning the thermometer comprises removing the adhesive layer covering and affixing the adhesive material layer to the tray.

8. The method of claim 1 wherein the washing cycle comprises in sequential order a first washing cycle, a second washing cycle, a third washing cycle, a fourth washing cycle, a fifth washing cycle, and a sixth washing cycle, wherein each washing cycle includes a desired medical washing temperature and wherein the method further comprising measuring the peak surface temperature for each washing cycle, wherein measuring the peak surface temperature for each washing cycle comprises removing the thermometer positioned for the first washing cycle and affixing a new thermometer prior to each subsequent washing cycle, wherein each thermometer is selected from a group of thermometers having different predefined thermometer temperature ranges such that the predefined temperature range of the selected thermometer corresponds with the desired medical washing temperature of the washing cycle.

9. The method of claim 8 wherein the first washing cycle is a cold water rinse cycle and the method further comprises selecting a thermometer having a thermometer temperature range comprises the range of 100° F. to 110° F. so that the peak surface temperature can be measured for use in preventing hemoglobin from baking on the medical device.

10. The method of claim 8 wherein the second washing cycle is an enzyme cycle and the method further comprises selecting a thermometer having a thermometer temperature range comprises the range of 110° F. to 130° F. so that the peak surface temperature can be measured for use in preventing prevent enzymes from become ineffective at breaking down proteins on the medical device.

11. The method of claim 8 wherein the third washing cycle is a detergent cycle and the method further comprises selecting a thermometer having a thermometer temperature range comprises the range of 140° F. to 150° F. so that the peak surface temperature can be measured for use in preventing the detergent cycle from becoming ineffective.

12. The method of claim 8 wherein the fourth washing cycle is a disinfection cycle and the method further comprises selecting a thermometer having a thermometer temperature range comprises the range of 170° F. to 180° F. so that the peak surface temperature can be measured for use in preventing the detergent cycle from becoming ineffective.

13. The method of claim 8 wherein the fifth washing cycle is an ultrasonic cycle and the method further comprises selecting a thermometer having a thermometer temperature range comprises the range of 100° F. to 110° F. if enzymes are used and 120° F. to 130° F. if alkaline detergent is used so that the peak surface temperature can be measured for use in preventing the ultrasonic cycle from becoming ineffective.

14. The method of claim 8 wherein the sixth washing cycle is a manual soaking cycle and the method further comprises selecting a thermometer having a thermometer temperature range comprises the range of 90° F. to 110° F. so that the peak surface temperature can be measured for use in preventing detergents or enzymes from becoming ineffective.

15. A method of calibrating a medical washing machine, the method comprising:
    inserting the medical device into the medical washing machine for a washing cycle, wherein inserting the medical device comprises placing the medical device on a tray and inserting the medical device and the tray into the washing machine at the same time;
    attaching an irreversible thermometer strip to the tray proximate the medical device;
    measuring a peak temperature of the medical device with the irreversible thermometer strip during the washing cycle
    removing the thermometer strip from the tray;
    calibrating the washing machine to execute the same washing cycle at a different temperature if the measured peak temperature is different than a desired peak temperature for the washing cycle; and
    attaching another irreversible thermometer strip to the tray to measure a second peak temperature of the washing cycle after calibrating the washing machine to verify whether the calibration of the washing machine successfully caused the washing machine to execute the same washing cycle at the desired peak temperature.

16. The method of claim 15 further comprising matching a material of the tray to a material of the medical device such that the material of the tray mimics the material of the medical device.

* * * * *